US009271896B2

(12) United States Patent
Clements (10) Patent No.: US 9,271,896 B2
(45) Date of Patent: Mar. 1, 2016

(54) APPARATUS FOR WEIGHT BASED SINGLE DOSES OF MEDICATION

(71) Applicant: David Clements, San Francisco, CA (US)

(72) Inventor: David Clements, San Francisco, CA (US)

( * ) Notice: Subject to any disclaimer, the term of this patent is extended or adjusted under 35 U.S.C. 154(b) by 0 days.

(21) Appl. No.: 14/311,289

(22) Filed: Jun. 21, 2014

(65) Prior Publication Data

US 2015/0366757 A1 Dec. 24, 2015

(51) Int. Cl.
*A61M 5/00* (2006.01)
*A61J 1/18* (2006.01)
*A61B 19/00* (2006.01)

(52) U.S. Cl.
CPC . *A61J 1/18* (2013.01); *A61B 19/44* (2013.01); *A61B 2019/442* (2013.01); *A61B 2019/444* (2013.01); *A61B 2019/446* (2013.01)

(58) Field of Classification Search
CPC ..... A61M 5/3129; A61M 5/31; A61M 5/178; A61M 5/002; B65D 25/34; B65D 2203/02; B65D 2203/00; G06F 19/30; A61B 19/026
USPC .......... 206/534, 459.5, 457, 459.1, 528, 438, 206/363, 370, 364; 604/506, 189; 40/633
See application file for complete search history.

(56) References Cited

U.S. PATENT DOCUMENTS

| | | | | |
|---|---|---|---|---|
| 3,299,891 A * | 1/1967 | Smeton | | 604/232 |
| 4,022,206 A * | 5/1977 | Hilleman et al. | | 604/197 |
| 4,857,716 A | 8/1989 | Gombrich et al. | | |
| 5,009,894 A * | 4/1991 | Hsiao | | 424/451 |
| 6,132,416 A | 10/2000 | Broselow | | |
| 6,276,533 B1 * | 8/2001 | Kaplan | | 206/534 |
| 6,357,626 B1 * | 3/2002 | Zhang et al. | | 222/78 |
| 6,581,773 B2 * | 6/2003 | Kaplan | | 206/534 |
| 6,764,469 B2 * | 7/2004 | Broselow | | 604/207 |
| 7,056,307 B2 | 6/2006 | Smith et al. | | |
| 7,083,606 B2 | 8/2006 | Fineberg | | |
| 8,479,919 B2 * | 7/2013 | Kaplan et al. | | 206/459.5 |
| 8,494,880 B2 * | 7/2013 | Tripoli | | 705/3 |
| 2001/0050242 A1 * | 12/2001 | Kaplan | | 206/534 |
| 2007/0119862 A1 * | 5/2007 | Backes et al. | | 222/94 |
| 2010/0181218 A1 * | 7/2010 | Beccaro et al. | | 206/365 |
| 2011/0257628 A1 * | 10/2011 | Hirai | | 604/506 |
| 2012/0006712 A1 * | 1/2012 | Kaplan et al. | | 206/459.5 |
| 2012/0061286 A1 * | 3/2012 | Hueb De Menezes Oliveira et al. | | 206/571 |
| 2012/0145579 A1 * | 6/2012 | Silvano | | 206/459.5 |
| 2013/0015204 A1 * | 1/2013 | Gol | | 222/129 |
| 2013/0018326 A1 | 1/2013 | Hooven | | |
| 2013/0204225 A1 | 8/2013 | Creaturo | | |
| 2013/0299381 A9 * | 11/2013 | Luciano, Jr. | | 206/534 |

OTHER PUBLICATIONS

"PediaCare Single Dosage" article, Roubinek Reality. Dated Oct. 14, 2013. http://www.roubinek.net/what-you-need-to-know-about-fevers-and-how-pediacare-can-help/pediacare-single-dosage/.*

* cited by examiner

*Primary Examiner* — Steven A. Reynolds
(74) *Attorney, Agent, or Firm* — Ariel S. Bentolila; Bay Area IP Group LLC (57) ABSTRACT

An apparatus having a container comprising a volume. The volume is configured to retain a single dose of a medication appropriate for a specific classification of a weight of a patient. A first indicia is disposed on an exterior surface of the container. The first indicia indicates a type of the medication. A second indicia is disposed on the exterior surface. The second indicia indicates the specific classification, wherein the container, pre-packaged with the single dose, is appropriate for a single use dosing of the patient having the specific classification.

20 Claims, 5 Drawing Sheets

APPARATUS FOR WEIGHT BASED SINGLE DOSES OF MEDICATION

CROSS-REFERENCE TO RELATED APPLICATIONS

Not applicable.

RELATED CO-PENDING U.S. PATENT APPLICATIONS

Not applicable.

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office, patent file or records, but otherwise reserves all copyright rights whatsoever.

FIELD OF THE INVENTION

One or more embodiments of the invention generally relate to pharmaceuticals. More particularly, the invention relates to weight based premeasured single doses of pediatric medication.

BACKGROUND OF THE INVENTION

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon. Medication errors and dosing errors in particular are believed to be a large problem in medical settings. Due to the point that the size of pediatric patients can vary greatly depending on the age of the patient, one may expect that these errors may be especially problematic in the pediatric population. For example, without limitation, a 1 week old may be half the size of a 6 month old and a fraction the size of a 5 year old. Therefore, a medication dose for a 5 year old may likely be lethal for a 1 week old. Furthermore, it is contemplated that the rate of medication errors may be made worse depending on the situation in which the medications are being given. For example, without limitation, error rates in pre-hospital patients treated by EMS services or in emergency and resuscitation situations in hospitals may likely be greater than error rates for patients in non-emergency, hospital situations. Moreover, it is contemplated that the risk of negative outcomes as a result of medication errors may increase during an emergency as many of the drugs administered during an emergency are high-alert medications and patients are often in a vulnerable state.

Medication dosage errors in pediatric patients are largely attributable to the need to calculate weight based dosages. If an adult is being resuscitated, most of the first line drugs given emergently are typically in prefilled syringes containing a single dose. For example, without limitation, if a physician requests epinephrine, a nurse is usually able to take an epinephrine syringe from an emergency drawer and inject the entire contents through the patient's IV. This single dose is normally the correct dose for almost all adults. In contrast, most medications for pediatric patients are typically provided in containers or vials that have a large concentrated dose of medication from which the recommended dose is drawn. In an emergency situation, a pediatric patient's weight is estimated using a conventional method such as, but not limited to, basing the weight on the age of the patient or utilizing a measuring tape that uses length, body surface area, limb measurements or a combination to estimate the patient's size. Then, a pediatric medication chart is typically used to determine the appropriate dose of the specific medication for a child of that size. In some cases, the medication dose may need to be converted from the concentration of the vial containing a larger dose of the medicine, drawn up, and finally given to the patient. Additionally, the various different medications that may be requested by the physician, of which there are many, may each have a unique concentration, dose, volume, etc. Often these calculations can be complex. Due to the potential complexity of this process, one may expect that treatment may be delayed or that mistakes may be made. In addition, calculating dosages may cause additional stress for personnel or the patient during an emergency situation. Currently, it is believed that there is no way to avoid performing calculations to administer the correct dose of most pediatric medications, even in a relaxed non-urgent situation. For example, to administer ibuprofen to a pediatric patient, the doctor first determines how many milligrams (mg) per kilogram to give to the patient, and the medication is ordered as a mg dose. The ibuprofen is typically provided in a concentrated dose of say 100 milligrams in 5 milliliters. Therefore, the medical staff must then calculate the volume of the liquid to administer to the patient.

The following are examples of specific aspects in the prior art that, while expected to be helpful to further educate the reader as to additional aspects of the prior art, is not to be construed as limiting the present invention, or any embodiments thereof, to anything stated or implied therein or inferred thereupon. By way of educational background, an aspect of the prior art generally useful to be aware of is that current solutions to administering the appropriate dose of many medications to a pediatric patient, particularly in an emergency or resuscitation situation, typically require the medical personnel to perform calculations or to prepare the medication to some degree. For example, one current solution involves a concept to reconstitute all pediatric resuscitation medications into a standardized formulation/concentration so that the dose of all of these medications is the same volume for a given weight range. Using this method the medical personnel estimates the weight of the patient and then calculates the volume of medication that would be an appropriate dose for any of the medications made in this standardized concentration. Another current solution involves using a measuring tape to estimate the weight of the patient based on their length. Then a color associated with a child of that size is assigned to the patient. Once a color for a patient has been determined, this color may be used to formulate all of the dosage calculations for that patient. For example, if a patient is indicated by the measurements to fall into the blue category, a list of the appropriate dosages of multiple medications may be found on the blue page in a medication folder. However, the medication dose typically must still be calculated and drawn up. Furthermore, problems may arise if a member of the medical team is color blind. There may also be problems of continuity if, for example, the ambulance company uses this system and the receiving hospital does not or vice versa.

In view of the foregoing, it is clear that these traditional techniques are not perfect and leave room for more optimal approaches.

BRIEF DESCRIPTION OF THE DRAWINGS

The present invention is illustrated by way of example, and not by way of limitation, in the figures of the accompanying drawings and in which like reference numerals refer to similar elements and in which.

Unless otherwise indicated illustrations in the figures are not necessarily drawn to scale.

DETAILED DESCRIPTION OF SOME EMBODIMENTS

The present invention is best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will now be described in detail with reference to embodiments thereof as illustrated in the accompanying drawings.

From reading the present disclosure, other variations and modifications will be apparent to persons skilled in the art. Such variations and modifications may involve equivalent and other features which are already known in the art, and which may be used instead of or in addition to features already described herein.

Although Claims have been formulated in this Application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The Applicants hereby give notice that new Claims may be formulated to such features and/or combinations of such features during the prosecution of the present Application or of any further Application derived therefrom.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

Headings provided herein are for convenience and are not to be taken as limiting the disclosure in any way.

The enumerated listing of items does not imply that any or all of the items are mutually exclusive, unless expressly specified otherwise.

The terms "a", "an" and "the" mean "one or more", unless expressly specified otherwise.

Devices or system modules that are in at least general communication with each other need not be in continuous communication with each other, unless expressly specified otherwise. In addition, devices or system modules that are in at least general communication with each other may communicate directly or indirectly through one or more intermediaries.

A description of an embodiment with several components in communication with each other does not imply that all such components are required. On the contrary a variety of optional components are described to illustrate the wide variety of possible embodiments of the present invention.

As is well known to those skilled in the art many careful considerations and compromises typically must be made when designing for the optimal manufacture of a commercial implementation any system, and in particular, the embodiments of the present invention. A commercial implementation in accordance with the spirit and teachings of the present invention may configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

It is to be understood that any exact measurements/dimensions or particular construction materials indicated herein are solely provided as examples of suitable configurations and are not intended to be limiting in any way. Depending on the needs of the particular application, those skilled in the art will readily recognize, in light of the following teachings, a multiplicity of suitable alternative implementation details.

One embodiment of the present invention may provide weight based, prepackaged pediatric medications comprising a single dose of medication that may be uniquely appropriate for a specific patient weight or weight range. This embodiment may enable medical personnel to administer an appropriate dose of medication without the need to measure, scale, calculate, or draw up the dose as these medications may be available from the manufacturer in pre-measured doses with corresponding patient weights indicated on the containers. In some embodiments, the entire contents of the medication container may be the appropriate dose for a patient whose weight corresponds to the weight indicated on the container. By typically eliminating the need to calculate, measure, or draw up pediatric medications, it is believed that some embodiments of the present invention may help in reducing or practically eliminating medication dosing errors. Furthermore, some embodiments may ensure that medication is administered in a timely manner and may help to reduce stress on medical staff.

Figure 1:
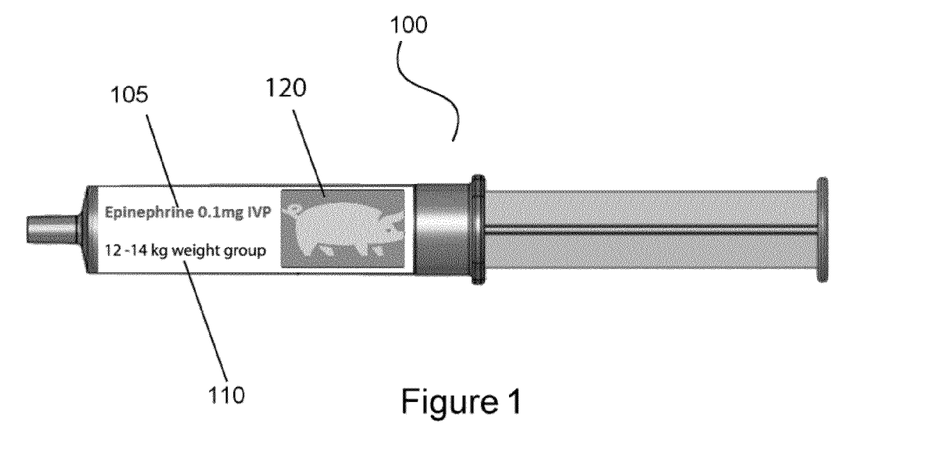
FIG. 1 is a diagrammatic side view of an exemplary syringe comprising a premeasured dose of medication for a pediatric patient, in accordance with an embodiment of the present invention.

FIG. 1 is a diagrammatic side view of an exemplary syringe 100 comprising a premeasured dose of medication for a pediatric patient, in accordance with an embodiment of the present invention. In the present embodiment, syringe 100 comprises an appropriate dose of Epinephrine for a child weighing between 12-14 kg as indicated by a drug label 105 and a patient weight classification 110. Some existing weight ranges for dosing pediatric patients in emergency situations are 3-5 kg, 6-7 kg, 8-9 kg, 10-11 kg, 12-14 kg, 15-18 kg, 19-23 kg, 24-29 kg, 30-36 kg. These weight ranges may be used generally or narrowed further to give more accurate dosing, particularly in the lower ranges. For example, the 3-5 kg range may be further reduced to 3 kg, 4 kg, 5 kg or smaller. It is anticipated the specific weight ranges used for the implementation of this invention may be decided by a panel of Pediatric Medical and Pharmaceutical experts. Some embodiments may be implemented to incorporate more or fewer weight groups. In the present embodiment, there may be a different single dose syringe or another type of container to coincide with each of these weight ranges. For example, without limitation, if a patient falls into the 12-14 kg weight range, the medical personnel may have access to a variety of medications in syringes or other types of containers in premeasured doses for a child of that weight. For practically every medication that may be given to a pediatric patient, there may be dispensing devices such as, but not limited to, syringes, medication cups, tablets, suppositories, drops, nebulizers or IV bags that comprise premeasured doses of a these medications, each of which is appropriate for a specific weight group. Medications that may be provided in these premeasured, single dose containers may include, without limitation, all common medications that may be administered in emergency or resuscitation situations and in non-emergency situations, as well as chemotherapy drugs, dialysis treatments, IV contrasts and dyes for radiology, etc. Some of these medications may include, but are not limited to, epinephrine, atropine, lidocaine hydrochloride, etomidate, midazolam, ketamine, fentanyl citrate, morphine sulfate, thiopental sodium, succinylcholine chloride, pancuronium bromide, vecuronium bromide, lorazepam, diazepam, naloxone, adenosine, calcium gluconate, dextrose, sodium bicarbonate, phenobarbital sodium, ibuprofen, acetaminophen, etc. In some embodiments, blood and blood products may also be prepackaged in such a way that the volume of the blood matches the correct volume required for the weight range of the child. Some embodiments may be configured to administer medications to adults when doses may vary depending on various different factors such as, but not limited to weight, age, sex, condition, etc. Other embodiments may be implemented for use in a multiplicity of suitable applications including, without limitation, veterinary applications, etc.

Figure 6:
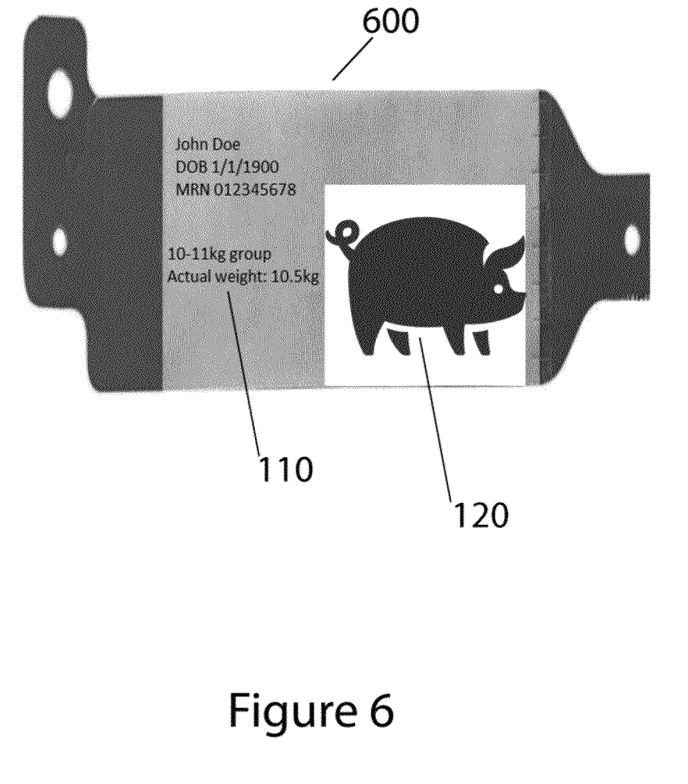
FIG. 6 illustrates an exemplary wrist band, in accordance with an embodiment of the present invention.

In the present embodiment, syringe 100 may be clearly marked with the name of the medication with drug label 105 and the patient weight range for which the dose is appropriate by weight classification 110. Similar markings may be placed on the container regardless of the type of container. For example, without limitation, the name and weight range may be clearly marked on single dose medication cups, IV bags, etc. In some embodiments the medication container may comprise a variety of additional or different information such as, but not limited to, the actual dosage of the medication, any legally mandated indicia, warnings, possible side effects, etc. In some embodiments the weight range may be shown in multiple or different units of weight including, without limitation, kilograms, pounds, ounces, etc. It is contemplated that in some embodiments, weight classification 110 may comprise various different types of indicators 120 in addition to or rather than the written form of the weight range to indicate which weight range may be given that specific dose. For example, without limitation, each weight group may be identified by an image of a unique animal. In this case perhaps an image of a cat may be used to represent a 6 kg weight group so that each syringe or container with the appropriate dose for a child weighing 6 kg comprises an image of a cat, regardless of the medication, volume of medication, method of administration of the medication, etc. As part of a system that may incorporate premeasured doses of pediatric medications, the patient may also be provided with a wrist band 600 (See FIG. 6), sticker or stamp etc comprising an image of a cat, which may be checked against the indicator 120 on the medication being dispensed to generally ensure the correct dose is administered. Alternatively, as illustrated by way of example in FIG. 2, the container may be colored to correspond to a color code representing various weight ranges. Similarly, the patient may wear a wrist band of the same color to check against the medication containers. Those skilled in the art will readily recognize, in light of and in accordance with the teachings of the present invention, that a multiplicity of suitable indicators 120 may be used to associate the container to a specific weight range such as, but not limited to, cartoon characters, animals, shapes, letters, numbers, names, symbols, etc. In addition, scales incorporating the specific weight ranges and associated indicator into their measurements may also be implemented to further ensure that the correct weight range is determined for the patient. For example, without limitation, when a patient is weighed on such a scale, the weight of the patient may be displayed as well as the indicia used to differentiate that weight range, e.g., a color or an image of an animal, etc.

Figure 2:
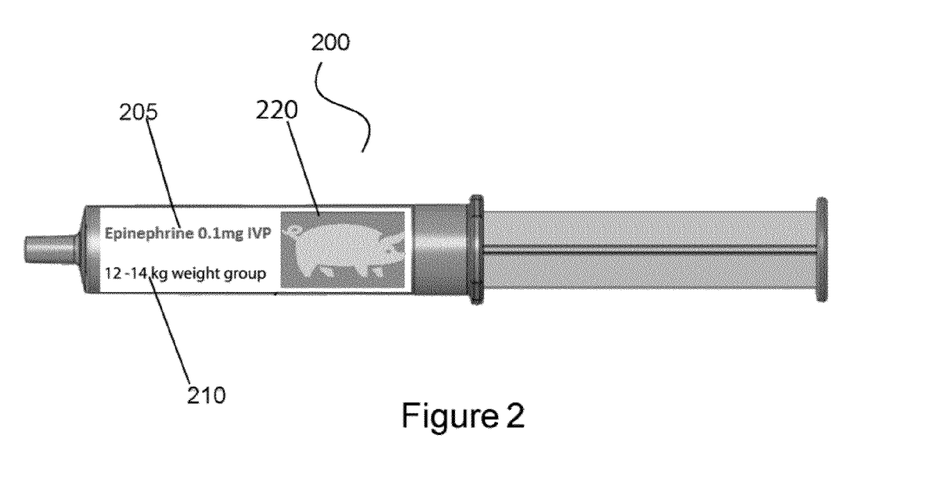
FIG. 2 is a diagrammatic side view of an exemplary color coded syringe comprising a premeasured dose of medication for a pediatric patient, in accordance with an embodiment of the present invention.

FIG. 2 is a diagrammatic side view of an exemplary color coded syringe 200 comprising a premeasured dose of medication for a pediatric medication, in accordance with an embodiment of the present invention. In the present embodiment, syringe 200 comprises an appropriate dose of Epinephrine for a child weighing between 12-14 kg as indicated by a drug label 205 and a patient weight classification 210. The body of syringe 200 is yellow to correspond to the weight range of 12-14 kg for which the dose of medication in syringe 200 is appropriate. It is contemplated that some embodiments using color coding may use different colors to represent different weight ranges. For example, without limitation, some embodiments may be configured to correspond to the color coding schemes of existing resuscitation systems such as, but not limited to, the Broselow system, the Antevy system, and any future systems that may be developed. Other embodiments may use a unique color coding system. In some embodiments the syringe or other medication container may comprise a dot or stripe of the color rather than being fully colored. In some embodiments, weight classification 210 may also incorporate the use of a weight range indicator 220 such as, but not limited to, an animal image in addition to the color coding.

Figure 3:
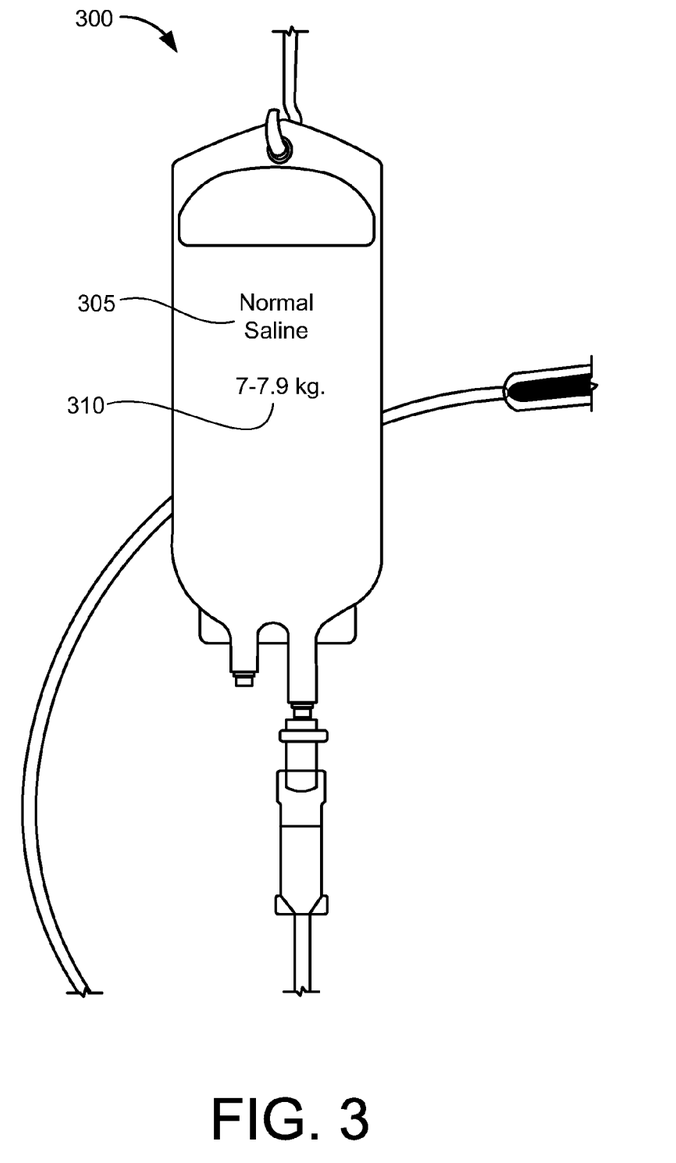
FIG. 3 is a diagrammatic front view of an exemplary IV bag containing normal saline comprising a premeasured dose of medication for a pediatric patient, in accordance with an embodiment of the present invention.

FIG. 3 is a diagrammatic front view of an exemplary IV bag 300 containing normal saline comprising a premeasured dose of medication for a pediatric patient, in accordance with an embodiment of the present invention. In the present embodiment, IV bag 300 comprises an appropriate dose of normal saline for a child within a certain weight (range), an example of which is shown for a child weighing between 7-7.9 kg as indicated by a drug label 305 and a patient weight classification 310.

Figure 4:
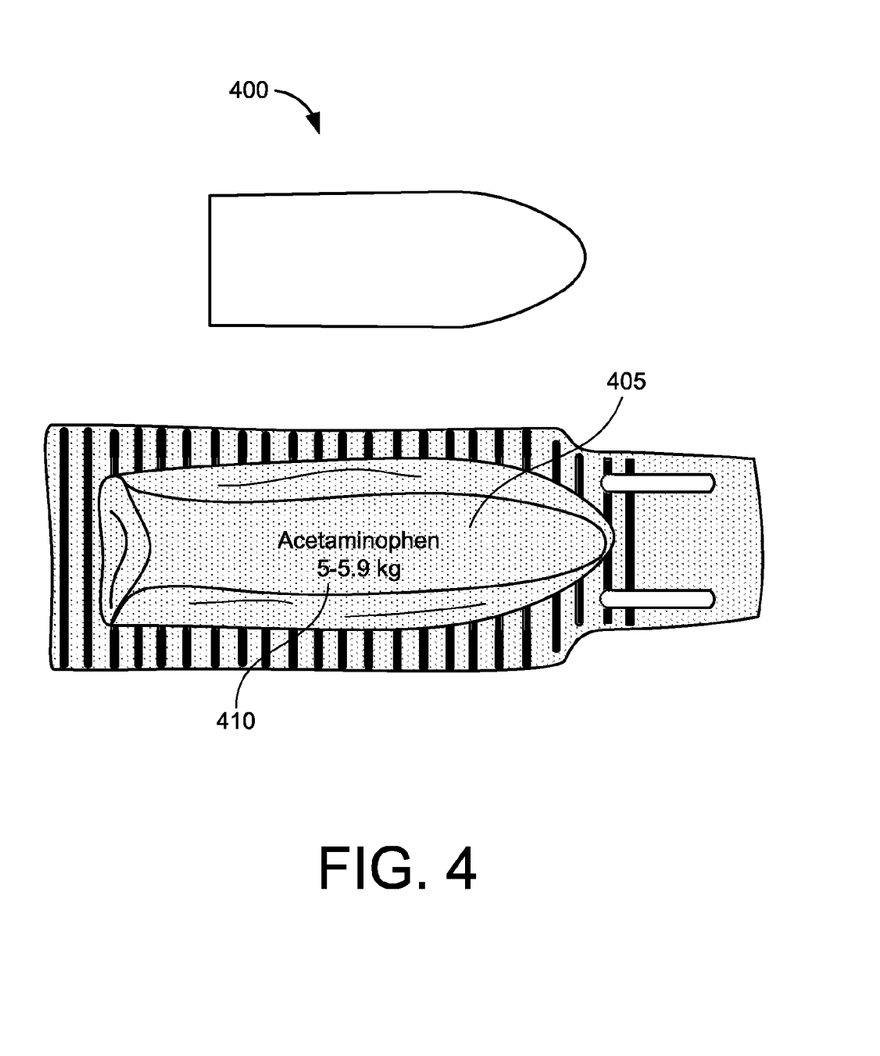
FIG. 4 is a diagrammatic front view of an exemplary suppository comprising a premeasured dose of medication for a pediatric patient in a certain weight class, in accordance with an embodiment of the present invention.

FIG. 4 is a diagrammatic front view of an exemplary suppository 400 comprising a premeasured dose of Acetaminophen for a pediatric patient in a certain weight class, in accordance with an embodiment of the present invention. In the present embodiment, suppository 400 comprises an appropriate dose of Acetaminophen for a child within a certain weight (range), an example of which is shown for a child weighing between 5-5.9 kg as indicated by a drug label 405 and a patient weight classification 410.

Figure 5:
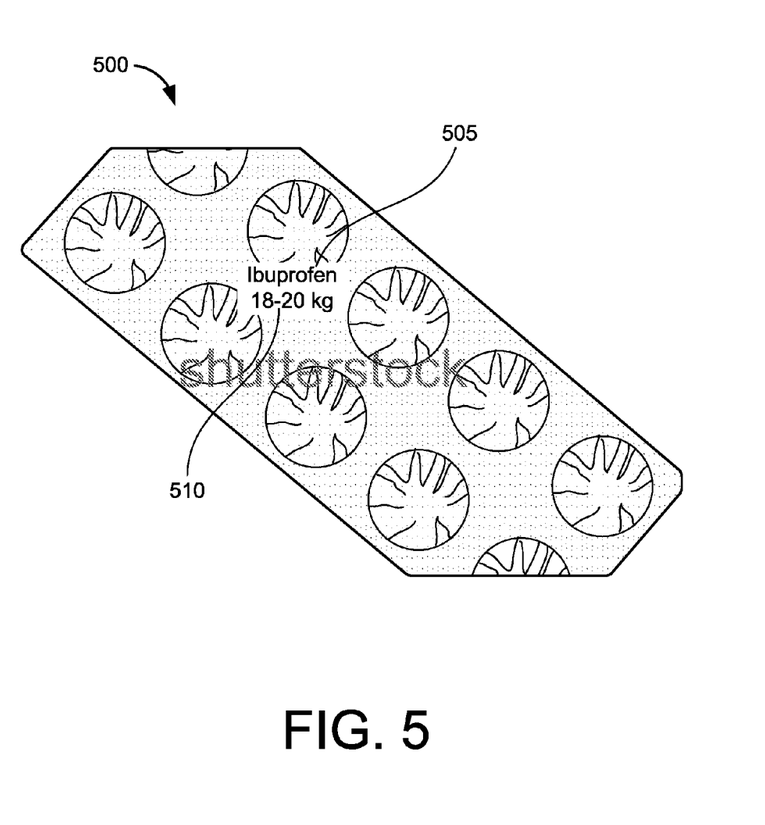
FIG. 5 is a diagrammatic back view of an exemplary blister pack comprising a premeasured dose of medication for a pediatric patient, in accordance with an embodiment of the present invention.

FIG. 5 is a diagrammatic back view of an exemplary blister pack 500 comprising a premeasured dose of Ibuprofen for a pediatric patient, in accordance with an embodiment of the present invention. In the present embodiment, blister pack 500 comprises an appropriate dose of Ibuprofen for a child within a certain weight (range), an example of which is shown for a child weighing between 18-20 kg as indicated by a drug label 505 and a patient weight classification 510.

In typical use of an embodiment of the present invention, the patient's weight is first obtained on a scale or estimated using a measuring tape or some other weight estimating device. Virtually any medication that may be administered to the patient and some other types of treatments such as, but not limited to, fluids, imaging dyes or contrasts, or nutritional supplements may be available to the medical personnel in premeasured, single dose containers corresponding to specific patient weight ranges. The medications in these containers may be given immediately to the patient typically without the need to perform dosing calculations or the need to draw up the medication from a larger vial or container. A doctor may order a pediatric medication as a standardized order based on the weight range of the patient. The order would typically correspond to the weight range indicated on a pre-measured, single dose syringe or another type of container. The nurse or other medical personnel may then be able to administer the medication quickly and easily by simply obtaining the medication in a premeasured, single dose container, ensuring that the weight range on the container is appropriate for the patient, and administering the entire dose to the patient. By administering the entire contents of the medication container, the nurse typically gives the patient the optimal dose of that medication for a child of that weight.

It is contemplated that, whenever possible, the single dose containers in which the medications are provided may be the dispensing device or final packaging for the medication. For example, without limitation, IV push meds may be provided in a syringe that may be administered directly into an IV without measuring or drawing up the medication. Oral medications may be provided in a syringe that can be squeezed into the patient's mouth or in a medication cup that can be sipped. IV fluids may be provided in a bag with the appropriate volume for the weight range. Where medications require reconstitution with a dissolving solution, for example, without limitation, antibiotics, both the medication in the vial holding the medication and the volume of the bag of dissolving solution may be provided in the appropriate dose to administer to the patient in full based on their weight range, with no waste or calculations required. Those skilled in the art will readily recognize, in light of and in accordance with the teachings of the present invention, that medications and treatments administered through various different means may incorporate single dose dispensing containers according to some embodiments of the present invention. Some non-limiting examples of these types of medications and treatments include but are not limited to, inhaled, iv bolus, iv fluids, iv infusion, intramuscular, oral, nebulized, sub cutaneous, sub lingual, topical, dermal, intradermal, transdermal, intraosseous, intra-articular, intranasal, urethral, vaginal, aural, ocular, nasal, suppositories, treatments administered through nasogastric tubes, gastric tubes, and feeding tubes etc. In some embodiments medications may be provided in premeasured single dose containers that are not dispensing devices, such as but not limited to, vials. In these embodiments, the appropriate dose of the medication for that patent may be premeasured, yet the medication may still need to be drawn up into a dispensing container such as, but not limited to, a syringe or otherwise prepared to be administered.

The use of premeasured single dose medication containers according to some embodiments of the present invention may help to prevent problems associated with medication dispensing errors during pediatric medication dispensing generally and pediatric resuscitation especially. The single dose containers may also help to ensure that the patient typically receives the medication in a timely fashion as no calculations need to be made or medications drawn up from a vial. The ease of administration of medications in single dose containers may also reduce stress on the medical staff, especially during emergencies. Furthermore, medication ordering may be easier for doctors, and medication administration may be easier for nurses and other medical personnel. In addition, research into medications and methods may be unreliable due to improper dosing when using current dosing methods. This issue may be reduced or eliminated with the use of some embodiments since researchers may be more confident in the data they were receiving because of more accurate dosing.

For safety reasons, some embodiments may incorporate a system to hold these pre-dosed medications, with each weight group having their own unique drawer or container. For example, without limitation, a mobile cart with multiple drawers may be used with a unique drawer or container for each weight range that holds only syringes and other drug containers with appropriate dosing for that weight range, similar to a pediatric resuscitation cart. In some embodiments each drawer or container may be color coded to correspond to existing resuscitation color codes such as the Broselow system or the Antevy system, or other weight range color coding systems. Within each drawer or container there may be at least one single dose container for multiple medications. The single dose containers may be clearly marked with the name of the drug and the weight range. The single dose containers may also comprise other information such as, but not limited to, actual dosage, color coding, side effects etc. For further safety, each medication may have a separate compartment within each drawer, which is clearly labelled with the name of the medication. In emergency situations it is specifically anticipated that this system may be used in conjunction with existing or future pediatric resuscitation or emergency systems including but not limited to the Broselow system, the Broselow Luten system, the Broselow Hinkle system, the Pediatric cart, the Broselow pediatric cart, the Artemis system, the Antevy system, the Mercy tape, etc. Some embodiments may use a multiplicity of suitable systems for holding and organizing pre-dosed medication such as, but not limited to, a cupboard or cabinet, an automated medication dispenser, a shelving system, refrigerated storage, a moveable trolley, a carry bag etc.

Those skilled in the art will readily recognize, in light of and in accordance with the teachings of the present invention, that some embodiments of the present invention may be used in almost any medical environment including, without limitation, doctors' offices, ambulances, hospitals, clinics, etc. Moreover, some embodiments may be configured for over the counter medications such as, but not limited to, ibuprofen, acetaminophen, antihistamines, etc. It is contemplated that medications provided in premeasured single dose containers may be closely integrated into the hospital or medical environment's pharmacy system. For resuscitation situations the medications may be kept in a cart beside an existing pediatric resuscitation cart or in the pediatric resuscitation cart. Medications specifically for resuscitations and emergencies and intended to be used in conjunction with existing resuscitation systems may be sold to service the systems, as part of the systems, as accessories to the systems, or as alternatives to the systems. In a non-emergency environment such as, but not limited to, an ER with a non-emergent presentation or a wellness clinic, there may be a medicine dispensing device such as, but not limited to, an Omnicell® system, which is like an electronic cupboard or vending machine that houses and dispenses a range of medications. It is envisioned that some embodiments may incorporate a separate Omnicell® type system or a separate cupboard for weight based, pre-dosed pediatric medications, which is clearly marked as such. It is contemplated that automated medication dispensing devices with greater capacity may be implemented to dispense pre-dosed medications, as providing a separate container for each individual dose may greatly increase the spacial storage requirement. If a patient is being treated on a hospital floor or in a hospital ward, nurses often perform medication rounds with a mobile cart that may be rolled from patient to patient to administer meds to the patients as needed. It is anticipated in this situation that this medication cart may comprise clearly delineated sections or drawers for each unique weight group of medications. Alternatively, a stationary automated dispensing unit or cupboard may be present on the floor or ward.

On an ambulance it is envisioned that premeasured single dose medication containers according to some embodiments may be incorporated into a system like the Broselow Hinkle system with multiple colored pouches that correspond to weight rages and where each pouch comprises pre-dosed containers of a range of medications that may be likely to be administered on an ambulance. Due to the lack of space on an ambulance, it may be desirable for the pouches to be small enough to be non-intrusive yet contain enough medications as necessary. In some embodiments these medication pouches may be collapsible and/or foldable. A doctor's office may use any of the above described methods or combinations of methods to incorporate single dose medication containers into their practice. In some embodiments, premeasured single doses of medication may be sold over the counter. Once the general public has been educated, medications may be stocked in drug stores or pharmacies in marked boxes or containers clearly stating that the doses contained inside are for children of a specific weight only. The packaging may also comprise a unique indicia such as, but not limited to, a color or an image so that consumers can easily identify the correct dosage. To aid in this, scales may be provided near the medications to verify the weight of the child before choosing a dosage.

Those skilled in the art will readily recognize, in light of and in accordance with the teachings of the present invention, that a multiplicity of suitable products and accessories may be developed for use with some embodiments. Computer program's may be produced or updated for doctors and hospitals that uses default settings to automatically populate the appropriate dose for a patient once the medication is chosen and the patient's weight is known. For example, without limitation, if a patient is 4.3 kg and the doctor wants to order ibuprofen, the program may automatically default to a 4 kg pre-dosed syringe order. Also, medication pumps may be developed or updated specifically for use with these pre-dosed medications. Some non-limiting examples of other products that may be developed for use with systems according to some embodiments may include, without limitation, a barcode reader that may scan barcodes on medication containers and on patient wristbands or files to confirm the correct dose is being administered, color coded IV ports, scales incorporating weight group specific indicia, medication holding and dispensing machines, wristbands to identify the child to its allocated weight group and corresponding indicia etc.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

It is noted that according to USA law 35 USC §112 (1), all claims must be supported by sufficient disclosure in the present patent specification, and any material known to those skilled in the art need not be explicitly disclosed. However, 35 USC §112 (6) requires that structures corresponding to functional limitations interpreted under 35 USC §112 (6) must be explicitly disclosed in the patent specification. Moreover, the USPTO's Examination policy of initially treating and searching prior art under the broadest interpretation of a "mean for" claim limitation implies that the broadest initial search on 112(6) functional limitation would have to be conducted to support a legally valid Examination on that USPTO policy for broadest interpretation of "mean for" claims. Accordingly, the USPTO will have discovered a multiplicity of prior art documents including disclosure of specific structures and elements which are suitable to act as corresponding structures to satisfy all functional limitations in the below claims that are interpreted under 35 USC §112 (6) when such corresponding structures are not explicitly disclosed in the foregoing patent specification. Therefore, for any invention element(s)/structure(s) corresponding to functional claim limitation(s), in the below claims interpreted under 35 USC §112 (6), which is/are not explicitly disclosed in the foregoing patent specification, yet do exist in the patent and/or non-patent documents found during the course of USPTO searching, Applicant(s) incorporate all such functionally corresponding structures and related enabling material herein by reference for the purpose of providing explicit structures that implement the functional means claimed. Applicant(s) request(s) that fact finders during any claims construction proceedings and/or examination of patent allowability properly identify and incorporate only the portions of each of these documents discovered during the broadest interpretation search of 35 USC §112 (6) limitation, which exist in at least one of the patent and/or non-patent documents found during the course of normal USPTO searching and or supplied to the USPTO during prosecution. Applicant(s) also incorporate by reference the bibliographic citation information to identify all such documents comprising functionally corresponding structures and related enabling material as listed in any PTO Form-892 or likewise any information disclosure statements (IDS) entered into the present patent application by the USPTO or Applicant(s) or any 3rd parties. Applicant(s) also reserve its right to later amend the present application to explicitly include citations to such documents and/or explicitly include the functionally corresponding structures which were incorporate by reference above.

Thus, for any invention element(s)/structure(s) corresponding to functional claim limitation(s), in the below claims, that are interpreted under 35 USC §112 (6), which is/are not explicitly disclosed in the foregoing patent specification, Applicant(s) have explicitly prescribed which documents and material to include the otherwise missing disclosure, and have prescribed exactly which portions of such patent and/or non-patent documents should be incorporated by such reference for the purpose of satisfying the disclosure requirements of 35 USC §112 (6). Applicant(s) note that all the identified documents above which are incorporated by reference to satisfy 35 USC §112 (6) necessarily have a filing and/or publication date prior to that of the instant application, and thus are valid prior documents to incorporated by reference in the instant application.

Having fully described at least one embodiment of the present invention, other equivalent or alternative methods of implementing premeasured single doses of pediatric medication according to the present invention will be apparent to those skilled in the art. Various aspects of the invention have been described above by way of illustration, and the specific embodiments disclosed are not intended to limit the invention to the particular forms disclosed. The particular implementation of the premeasured single doses of pediatric medication may vary depending upon the particular context or application. By way of example, and not limitation, the premeasured single doses of pediatric medication described in the foregoing were principally directed to implementations used in a medical setting; however, similar techniques may also be applied to the use of pre-dosed medications in various different settings such as, but not limited to, in the home, camps for children, schools or any setting where children may be, which implementations of the present invention are contemplated as within the scope of the present invention. The invention is thus to cover all modifications, equivalents, and alternatives falling within the spirit and scope of the following claims. It is to be further understood that not all of the disclosed embodiments in the foregoing specification will necessarily satisfy or achieve each of the objects, advantages, or improvements described in the foregoing specification.

Claim elements and steps herein may have been numbered and/or lettered solely as an aid in readability and understanding. Any such numbering and lettering in itself is not intended to and should not be taken to indicate the ordering of elements and/or steps in the claims.

The corresponding structures, materials, acts, and equivalents of all means or step plus function elements in the claims below are intended to include any structure, material, or act for performing the function in combination with other claimed elements as specifically claimed.

The Abstract is provided to comply with 37 C.F.R. Section 1.72(b) requiring an abstract that will allow the reader to ascertain the nature and gist of the technical disclosure. It is submitted with the understanding that it will not be used to limit or interpret the scope or meaning of the claims. The following claims are hereby incorporated into the detailed description, with each claim standing on its own as a separate embodiment.

What is claimed is:

1. An apparatus comprising:
    a container, said container comprising a volume, wherein said volume being configured to retain a premeasured single dose of a medication corresponding to a predetermined weight range of a patient, in which said container comprises a syringe prepackaged at the place of manufacture with said premeasured single dose medication being configured to eliminate the error or time needed to calculate, measure, or draw up said medication during an administration of said medication, and wherein said premeasured single dose medication is contained in said prepackaged syringe at the time of manufacture, before delivery or administering to said patient;
    a first indicia, said first indicia being disposed proximate an exterior surface of said syringe prepackaged at the place of manufacture, wherein said first indicia is configured to display a type of said premeasured single dose medication;

a second indicia, said second indicia being disposed on said exterior surface, wherein said second indicia is configured to display said predetermined weight range corresponding to said amount of said premeasured single dose medication, and wherein said container, pre-packaged with said premeasured single dose medication, is configured for a single use dosing of the patient having said predetermined weight range;

a wrist band, in which said wrist band comprising an approximate weight of said patient, wherein said wrist band is configured to check against said second indicia disposed on said single dose medication container being dispensed to generally ensure a correct dose is administered; and a weight range differentiator, in which said weight range differentiator comprising an image, wherein said weight range differentiator is configured to differentiate said predetermined weight range.

2. The apparatus as recited in claim 1, in which said patient is a child.

3. The apparatus as recited in claim 1, in which said weight range differentiator further comprising a sticker or a stamp being configured to check against said second indicia disposed on said medication container.

4. The apparatus as recited in claim 2, in which said single dose is configured to be administered to pediatric patients.

5. The apparatus as recited in claim 1, wherein said premeasured medication is a medication for pediatric patients.

6. The apparatus as recited in claim 5, in which said syringe comprises a color-code configured to correspond to said predetermined weight range.

7. The apparatus as recited in claim 1, in which said second indicia is an icon associated with said predetermined weight range.

8. The apparatus as recited in claim 7, in which said icon matches an icon on a patient's wristband to be associated with the patient.

9. The apparatus as recited in claim 8, in which said icon on said patient's wristband matches an icon displayed on a weight measuring device during weighing of the patient.

10. The apparatus as recited in claim 7, in which said icon further comprises an image of an animal.

11. The apparatus as recited in claim 1, in which said volume is further configured to retain an amount of fluid in which said medication is dissolved, wherein said amount of fluid is appropriate for a specific classification.

12. The apparatus as recited in claim 2, in which said single dose is configured to be administered for resuscitation situations.

13. The apparatus as recited in claim 12, in which the apparatus is configured for use in conjunction with color coding schemes for pediatric resuscitation.

14. The apparatus as recited in claim 13, in which said container is a color coded container configured to represent at least one weight range.

15. The apparatus as recited in claim 14, in which said color coding matches a color coding of said color coding schemes for pediatric resuscitation.

16. An apparatus consisting of:
means for retaining a premeasured single dose of a medication corresponding to a predetermined weight range of a patient, wherein said premeasured single dose medication being configured to eliminate the error or time needed to calculate, measure, or draw up said medication during an administration of said medication;

said retaining means comprising a syringe prepackaged at the place of manufacture with said premeasured single dose medication, and wherein said premeasured single dose medication is contained in said prepackaged syringe at the time of manufacture, before delivery or administering to said patient;

means for indicating a type of said premeasured single dose medication, wherein said means for indicating said premeasured single dose medication is disposed proximate an exterior surface of said prepackaged syringe;

means for indicating said predetermined weight range, wherein said retaining means, pre-packaged with said premeasured single dose medication at the time of manufacture, is appropriate for a single use dosing of the patient having said predetermined weight range;

means for checking against said indicating means on said retaining means being dispensed to generally ensure a correct dose is administered, in which said means for checking comprising a label with said weight range of said patient; and means for differentiating said predetermined weight range.

17. An apparatus comprising:
a dispensing device, said dispensing device comprising at least a syringe having a volume, wherein said volume being configured to retain a premeasured single dose of medication corresponding to a predetermined weight range of a child, in which said single dose is configured to be appropriate for pediatric situations, in which said dispensing device comprises a color coded syringe prepackaged at the place of manufacture being configured to administer said predetermined dosage of said medication, and wherein said premeasured single dose medication corresponding to said predetermined weight range of said child is contained in said prepackaged syringe at the time of manufacture before delivery or administering to said child;

a first indicia, said first indicia being disposed proximate an exterior surface of said color coded syringe, wherein said first indicia is configured to display a type of said premeasured single dose medication;

a wristband, in which said wristband comprising an approximate weight indicator of said patient, wherein said wristband is configured to check against said first indicia disposed on said single dose medication dispensing device being dispensed to generally ensure a correct dose is administered;

a second indicia, said second indicia being disposed on said exterior surface, in which said second indicia comprising a predetermined weight range associated with said first indicia, in which said second indicia generally matches said weight indicator on said wristband, in which said weight indicator on said wristband matches a measured weight displayed on a weight measuring device during weighing of a pediatric patient, wherein said color coded syringe, pre-packaged at the place of manufacture, with said single dose, is operable for a single use dosing of said pediatric patient; and a weight range differentiator, in which said weight range differentiator comprising an image disposed on a proximate exterior of said wrist band, wherein said image is configured to differentiate said predetermined weight range from a group of predetermined weight ranges.

18. The apparatus as recited in claim 17, in which said premeasured single dose medication is configured to be administered for resuscitation situations, wherein said premeasured single dose medication being configured to eliminate the error or time needed to calculate, measure, or draw up said medication during an administration of said medication.

19. The apparatus as recited in claim 18, in which said color coded syringe is configured to match a color coding scheme for pediatric resuscitations, in which said color coded syringe is further configured to generally ensure a correct dose is administered.

20. The apparatus as recited in claim 19, in which said wristband is color coded to match a color coding of said color coded syringe for pediatric resuscitations.

* * * * *